United States Patent
Steele (10) Patent No.: US 8,717,041 B2
(45) Date of Patent: May 6, 2014

(54) ANGLE MEASUREMENT DEVICE AND METHOD

(75) Inventor: Wilson F. Steele, Huntington Beach, CA (US)

(73) Assignee: Freedom Innovations, L.L.C., Irvine, CA (US)

( * ) Notice: Subject to any disclaimer, the term of this patent is extended or adjusted under 35 U.S.C. 154(b) by 402 days.

(21) Appl. No.: 13/015,442

(22) Filed: Jan. 27, 2011

(65) Prior Publication Data

US 2011/0199101 A1 Aug. 18, 2011

Related U.S. Application Data

(60) Provisional application No. 61/304,368, filed on Feb. 12, 2010.

(51) Int. Cl.
| | | |
|---|---|---|
| *G01B 7/30* | (2006.01) | |
| *A61F 2/64* | (2006.01) | |
| *G01D 5/20* | (2006.01) | |
| *A61F 2/76* | (2006.01) | |
| *A61F 2/68* | (2006.01) | |
| *A61F 2/70* | (2006.01) | |

(52) U.S. Cl.
CPC ............... *G01D 5/2013* (2013.01); *A61F 2/76* (2013.01); *A61F 2/68* (2013.01); *A61F 2002/704* (2013.01); *A61F 2/64* (2013.01)
USPC .......................... 324/654; 324/207.25; 623/40

(58) Field of Classification Search
CPC ........... G01D 5/2013; A61F 2/76; A61F 2/68; A61F 2002/704; A61F 2/64
USPC .................................. 324/654, 207.25; 623/40
See application file for complete search history.

(56) References Cited

U.S. PATENT DOCUMENTS

| | | | |
|---|---|---|---|
| 5,133,773 A | | 7/1992 | Sawamura et al. |
| 5,293,776 A | * | 3/1994 | Takegami et al. .......... 73/114.27 |
| 5,383,939 A | | 1/1995 | James |
| 5,571,205 A | | 11/1996 | James |
| 5,888,212 A | | 3/1999 | Petrofsky et al. |

(Continued)

FOREIGN PATENT DOCUMENTS

GB  2367753  4/2002

OTHER PUBLICATIONS

International Search Report and Written Opinion, dated Aug. 30, 2011, from PCT Application No. PCT/US2011/22753.

*Primary Examiner* — Jermele M Hollington
*Assistant Examiner* — Farhana Hoque
(74) *Attorney, Agent, or Firm* — Snell & Wilmer LLP (57) ABSTRACT

The present invention relates to a sensor device for determining an absolute angle of a prosthetic joint, and which is resistant to environmental elements and has a reduced power draw. The sensor device includes an inductive sensor and a rotatable member including a metal material. The metal material can include a non-ferrous metal material. The inductive sensor detects an amount of the metal material in a proximate location to the inductive sensor. Rotation of the rotatable member increases or decreases an amount of metal material in the proximate location of the inductive sensor. The amount of metal material in the proximate location corresponds to an angle of the rotatable member and the prosthetic joint based on a monotonic function. Thus, the inductive sensor detects the amount of metal material in the proximate location to determine the angle of the rotatable member and subsequently the angle of the prosthetic device.

20 Claims, 11 Drawing Sheets

(56) References Cited

U.S. PATENT DOCUMENTS

| | | |
|---|---|---|
| 6,113,642 A | 9/2000 | Petrofsky et al. |
| 6,423,098 B1 | 7/2002 | Biedermann |
| 6,517,585 B1 | 2/2003 | Zahedi et al. |
| 6,518,776 B2 | 2/2003 | Charneau et al. |
| 6,610,101 B2 | 8/2003 | Herr et al. |
| 6,673,117 B1 | 1/2004 | Soss et al. |
| 6,719,806 B1 | 4/2004 | Zahedi et al. |
| 6,740,125 B2 | 5/2004 | Mosler |
| 6,755,870 B1 * | 6/2004 | Biedermann et al. ........... 623/24 |
| 6,764,520 B2 * | 7/2004 | Deffenbaugh et al. ......... 623/24 |
| 7,055,383 B2 | 6/2006 | Kawakubo et al. |
| 7,810,621 B2 | 10/2010 | Zenno |
| 7,811,333 B2 | 10/2010 | Jónsson et al. |
| 2005/0189040 A1 * | 9/2005 | Rhodes et al. ................ 144/356 |
| 2006/0282175 A1 | 12/2006 | Haines et al. |
| 2007/0106396 A1 * | 5/2007 | Doddroe et al. ................ 623/52 |
| 2009/0319055 A1 * | 12/2009 | Iversen et al. .................. 623/49 |

\* cited by examiner

ANGLE MEASUREMENT DEVICE AND METHOD

CROSS-REFERENCE TO RELATED APPLICATIONS

The present application claims the benefit of U.S. Provisional Application Ser. No. 61/304,368 filed on Feb. 12, 2010 entitled "Angle Measurement Device and Method," which is hereby incorporated by reference in its entirety. The present application also incorporates by reference U.S. Pat. No. 7,655,050 and U.S. application Ser. No. 12/697,969, filed Feb. 1, 2010, each as if fully set forth herein.

BACKGROUND

1. Field of the Invention

This disclosure relates to sensors for determining an absolute angle of rotational objects in a prosthetic joint.

2. Description of the Related Art

Modern, computer controlled prosthetic devices have many advantages over conventional prosthetic devices. For example, computer controlled prosthetic devices can allow the amputees to walk with limited fear of stumbling or falling, allow amputees to lead a more active lifestyle, and improve the likelihood that amputees can realize their full economic potential. This is especially beneficial for the thousands of new amputees each year and the millions of existing amputees.

However, modern, computer controlled prosthetic devices are limited in some aspects due to the number of electrical parts. These limitations can include, for example, the shortened lifespan of its electrical parts, such as a sensor to measure an angle of a prosthetic joint, due to dust, moisture, or other environmental elements. The dust, moisture, and other environmental elements can also limit, for example, the type of activities that an amputee can perform while using the modern, computer controlled prosthetic devices. However, computer control of a joint during normal ambulation, or gait, requires robust and accurate sensors to provide input to the control strategy. These sensors could detect information such as joint position, knee angle, forces, weight bearing forces, ankle torque, knee torque, velocity, or acceleration.

Other limitations with the sheer number of electrical parts include the power draw. Naturally, increasing the number of electrical parts correspondingly increases the power required to operate the prosthetic device. One method to support this large increase in power draw is to increase the battery size. However, increasing the battery size increases the size and weight of the prosthetic device. This is undesirable since the prosthetic device should be the same length as the intact limb of the amputee. Thus, larger prosthetic devices may be undesirable for amputees that are shorter in height, especially children. Furthermore, the added weight can hinder the movements of the amputee, regardless of height. However, children may be especially impacted as they will not be as muscularly developed and may not be adept at handling the extra weight of the larger battery. Thus, any decrease in power consumption is beneficial to amputees because of the corresponding reduction in the size and weight of the prosthetic device.

Thus, there is a need for a sensor device for determining an absolute angle of a prosthetic joint, and which is resistant to environmental elements and has a reduced power draw.

SUMMARY

The present invention relates to a sensor device for determining an absolute angle of a prosthetic joint, and which is resistant to environmental elements and has a reduced power draw. The sensor device of the present invention includes an inductive sensor and a rotatable member including a metal material. The inductive sensor detects an amount of the metal material in a proximate location to the inductive sensor.

As the rotatable member is rotated, a gap between the metal material and the inductive sensor increases or decreases. This increase or decrease in the gap corresponds to an amount of metal material in the proximate location of the inductive sensor. The amount of metal material in the proximate location corresponds to an angle of the rotatable member and/or the prosthetic joint based on a monotonic function. The monotonic function can be, for example, an absolute monotonic function or a relative monotonic function. Thus, the inductive sensor can detect the amount of metal material in the proximate location to determine the angle of the rotatable member and subsequently the angle of the prosthetic device. When an absolute monotonic function is used such as when the sensor device is an absolute sensor device, no memory is used to remember a previous position and to calculate a current position based on a differential. An absolute sensor device reduces power consumption by having fewer components.

Since the metal material does not contact the inductive sensor, the inductive sensor can be better sealed to protect the inductive sensor and/or the metal material from the environmental elements. This can increase longevity of the inductive sensor and/or the metal material. In addition, it may allow the amputee to perform activities which may have previously been limited using other sensing modalities due to the fear of environmental exposure to the inductive sensor and/or the metal material such as construction, hiking, and various sports, especially those involving water.

The metal material can include a non-ferrous metal material. The use of the non-ferrous metal material is advantageous in that non-ferrous metal material can be lighter than ferrous metal material. Thus, the weight of the prosthetic joint can be reduced. The reduced weight of the prosthetic joint can allow smaller amputees to use prosthetic devices. In can also allow a person in general to expend less energy using the prosthetic device devices.

Furthermore, the inductive sensor can utilize less power than other conventional sensors. This reduction in power consumption can translate to a smaller battery size required for the prosthetic device. This can again reduce the weight of the prosthetic device.

In one embodiment, the present invention is a sensor device for a prosthetic joint including a rotatable member, a metal material connected to the rotatable member, and an inductive sensor configured to detect an amount of the metal material in a proximate location to the inductive sensor, and to generate an output corresponding to an angle of the rotatable member based on the amount of the metal material in the proximate location.

In another embodiment, the present invention is a sensor device for a prosthetic joint including a rotatable member, a non-ferrous metal material connected to the rotatable member, and an inductive sensor configured to detect an amount of the non-ferrous metal material in a spherical shape based on a location of the inductive sensor, and to generate an output corresponding to an angle of the rotatable member based on the amount of the metal material in the spherical shape, wherein the amount of the non-ferrous metal material in the spherical shape corresponds to the angle of the rotatable member based on an absolute or relative monotonic function.

In yet another embodiment, the present invention is a method for determining an angle of a rotatable member in a prosthetic joint including detecting, using an inductive sensor, an amount of metal material in a proximate location, and generating, using the inductive sensor, an output corresponding to an angle of the rotatable member based on the amount of the metal material in the proximate location.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which.

DETAILED DESCRIPTION

The detailed description of exemplary embodiments herein makes reference to the accompanying drawings and pictures, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

Figure 1:
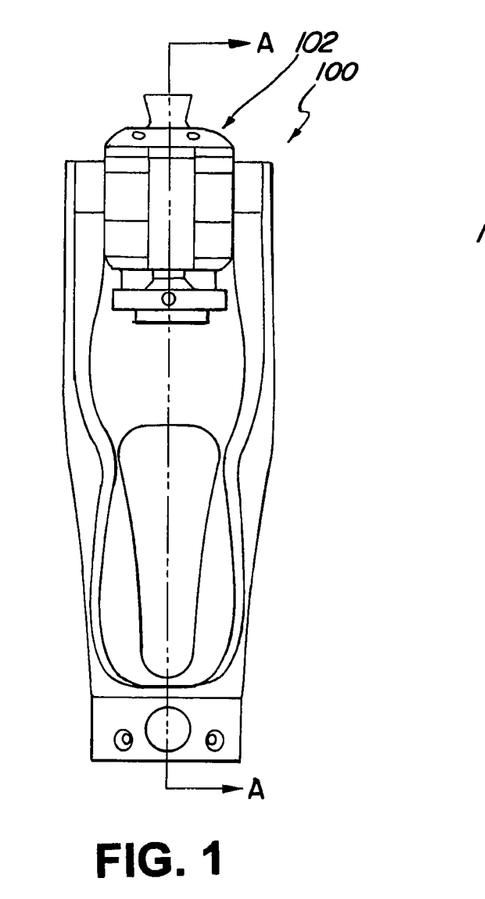
FIG. 1 depicts a frame of a prosthetic device according to an embodiment of the present invention.
Figure 2:
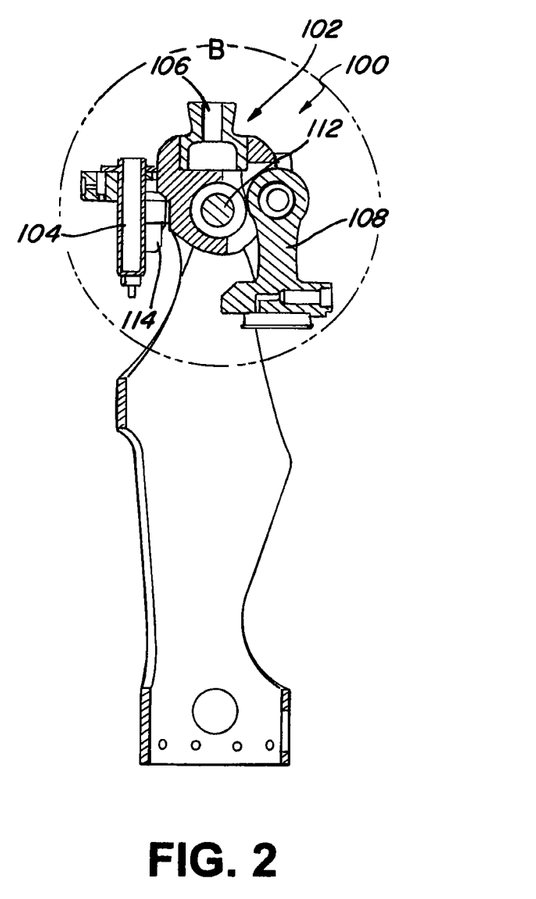
FIG. 2 is a sectional view of a prosthetic device according to an embodiment of the present invention.
Figure 3:
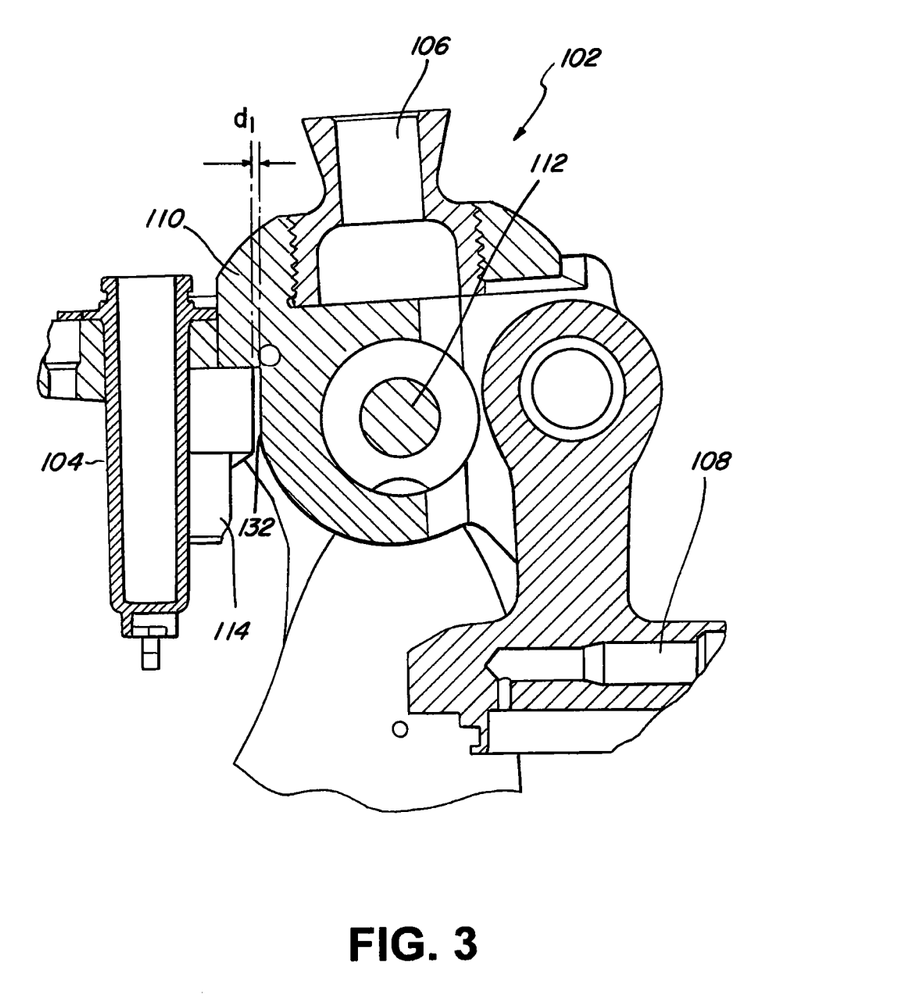
FIG. 3 depicts a prosthetic joint according to an embodiment of the present invention.

As shown in FIGS. 1 and 2, a prosthetic device 100 can include, for example, a prosthetic joint 102 and a frame 104. FIG. 2 depicts a cross-section of the prosthetic device 100 along the line A-A. The prosthetic joint 102 can be seen more clearly in FIG. 3, which is a close-up sectional view of portion B in FIG. 2. As seen in FIG. 3, the prosthetic joint 102 includes portions of the frame 104. The prosthetic joint 102 also includes, a rotatable member 106, a rotatable member 108 coupled to the rotatable member 106 such that rotation of the rotatable member 106 also rotates the rotatable member 108, and a metal portion 110 at an end of the rotatable member 106. The metal portion 110 can include, for example, a metal material and form, for example, a rotatable cam.

Figure 4:
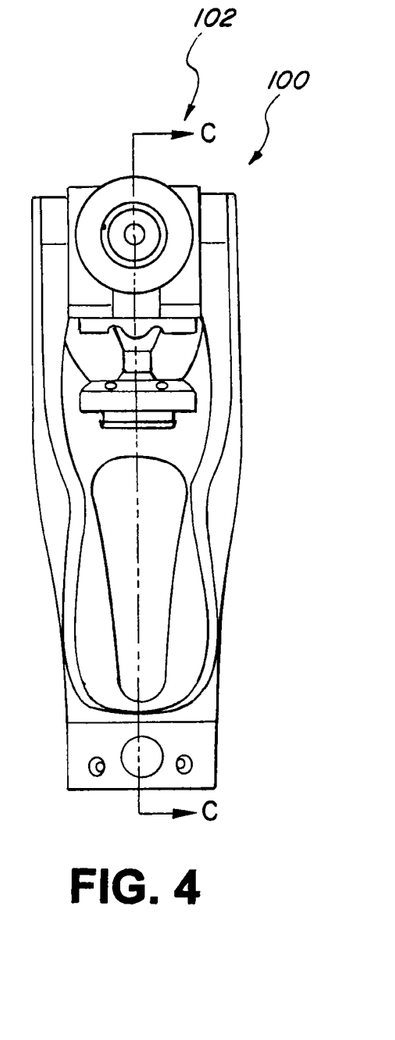
FIG. 4 depicts a prosthetic device according to an embodiment of the present invention rotated with respect to FIG. 1.
Figure 5:
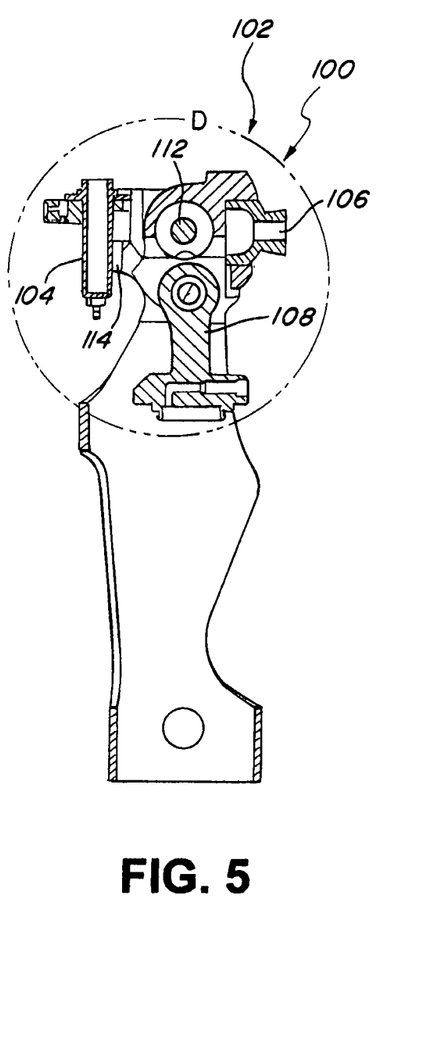
FIG. 5 is a sectional view of a prosthetic device according to an embodiment of the present invention rotated with respect to FIG. 2.
Figure 6:
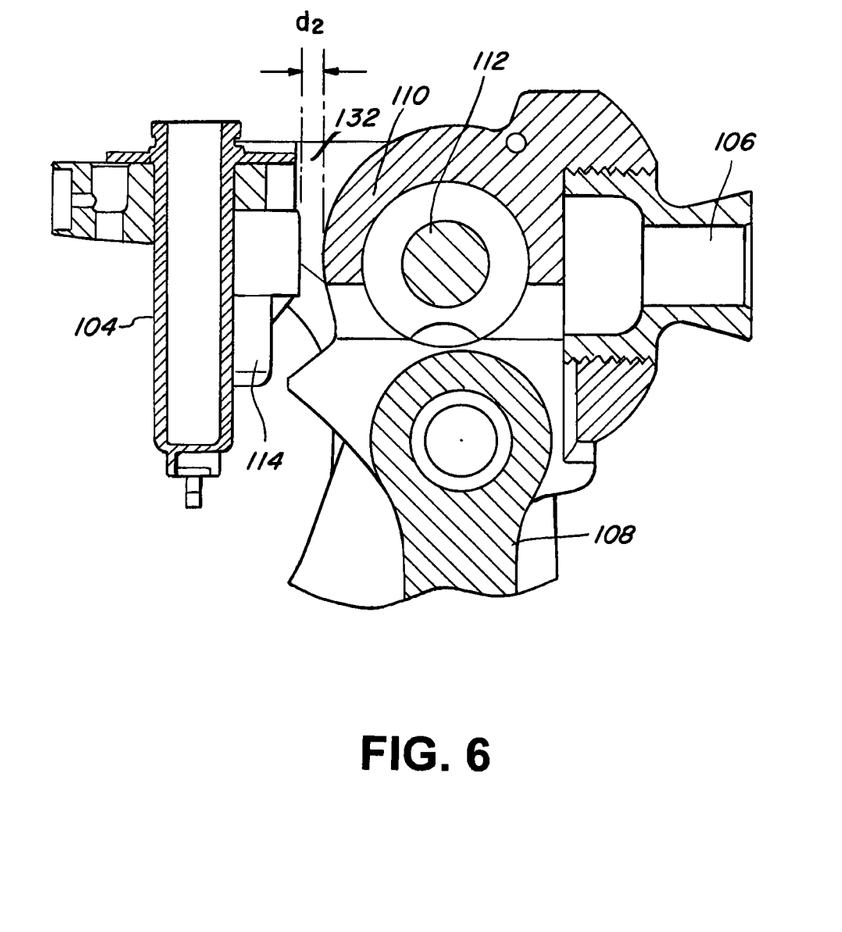
FIG. 6 depicts a prosthetic joint according to an embodiment of the present invention rotated with respect to FIG. 3.

The rotatable member 106 can rotate about a pivot 112 to move the prosthetic joint 102 into a different position. For example, in FIGS. 1-3, the prosthetic joint 102 and the rotatable member 106 are in a first position. However, FIG. 4 depicts the prosthetic joint 102 in a second position different than the first position. FIG. 5 depicts a cross-section of the prosthetic device 100 at the section C-C, while FIG. 6 depicts the section D indicated in FIG. 5. As seen in FIGS. 4-6, the prosthetic joint 102 and the rotatable member 106 have rotated onto the second position different from the first position.

Referring back to FIG. 3, the prosthetic device 100 includes a sensor 114 to determine the angle of the rotatable member 106 with respect to the prosthetic joint 102. The sensor 114 can be, for example, an inductive sensor which detects an amount of metal material in a proximate location to the sensor 114 and outputs metal material data regarding the amount of metal material in the proximate location.

One benefit of using an inductive sensor is the relatively low current draw. For example, the inductive sensor can utilize 6 µamps as opposed to some sensors which utilize thousands or even millions of µamps. This can significantly reduce a size of the battery required to operate the prosthetic device 100. A reduction in the battery size correspondingly reduces a size and weight of the prosthetic device. This allows for a more diverse type of amputee population to use the prosthetic device 100.

However, in one embodiment, the sensor 114 need not be limited to just inductive sensors. The sensor 114 can also be, for example, a capacitive sensor, a capacitive displacement sensor, and/or other type of appropriate sensor for determining an angle of the rotatable member 106.

Figure 7:
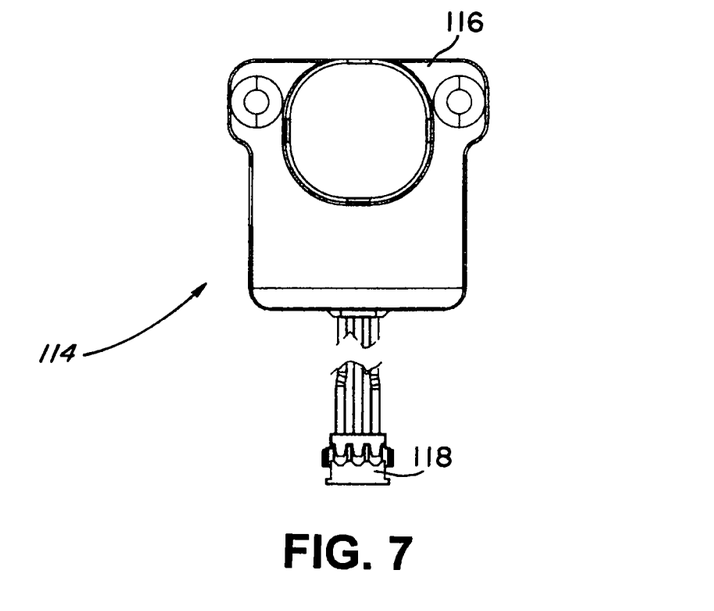
FIG. 7 depicts an inductive sensor according to an embodiment of the present invention.
Figure 8:
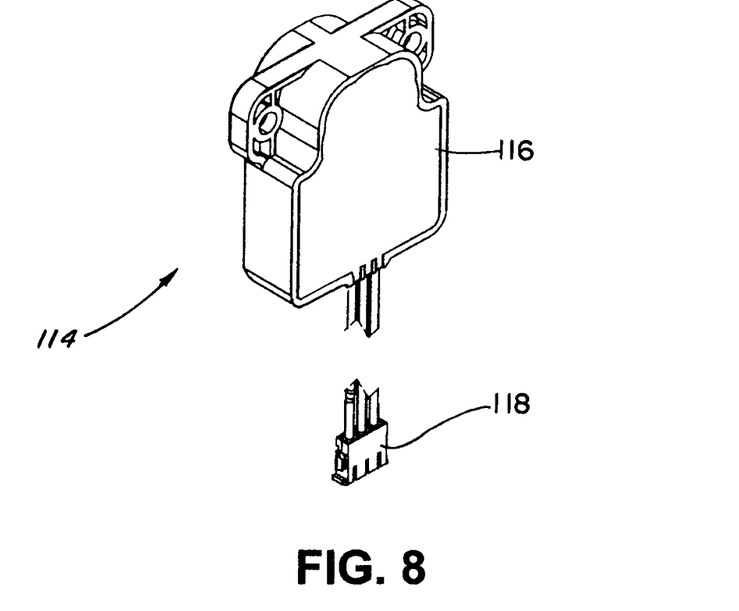
FIG. 8 is a perspective view of an inductive sensor according to an embodiment of the present invention.
Figure 9:
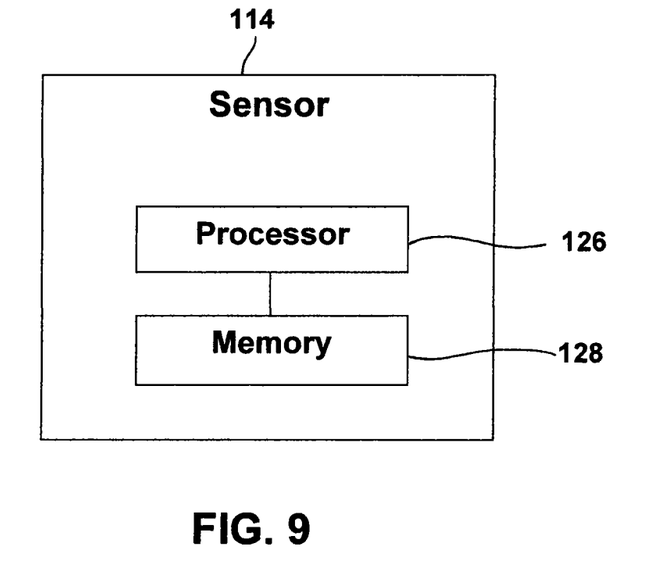
FIG. 9 depicts a sensor including a processor and a memory according to an embodiment of the present invention.

As seen in FIGS. 7 and 8, the sensor 114 can include, for example, a housing 116 and wires 118. The housing 116 can protect, for example the components of the sensor 114. The housing 116 can also form an environment seal to further protect the sensor 114 from damage. The wires 118 can transmit an output of the sensor 114 to a processor or other device which can analyze and/or manipulate the output of the sensor 114. In one embodiment, the sensor 114 can include, for example, a processor 126 and a memory 128 as shown in FIG. 9. The processor 126 can analyze the metal material data detected by the sensor 114, while the memory 128 can store information which can be used to analyze and/or manipulate the metal material data of the sensor 114.

Figure 10:
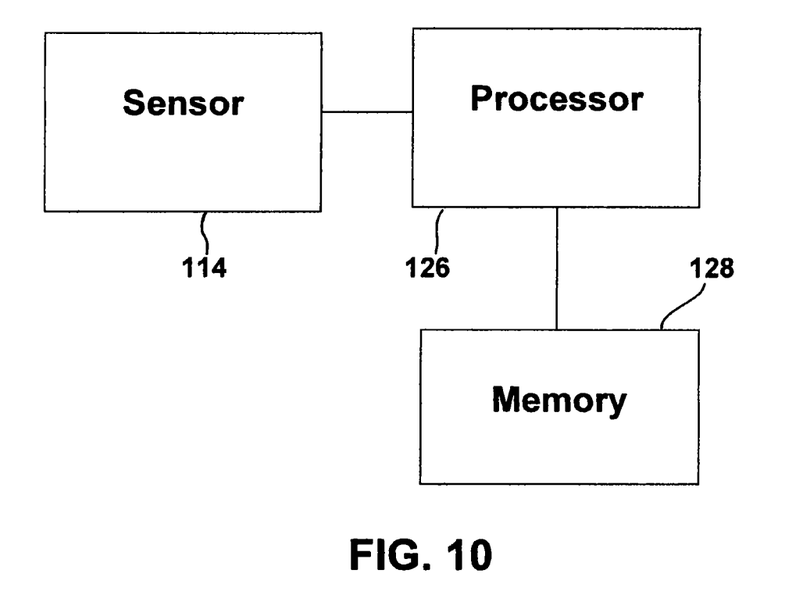
FIG. 10 is a box diagram of a sensor, a processor, and a memory according to an embodiment of the present invention.

In another embodiment, the processor 126 and the memory 128 are external to the sensor 114 as shown in FIG. 10. In which case, the sensor 114 can output the metal material data and the processor 126 can analyze and/or manipulate the metal material data using information stored in the memory 128.

Figure 11:
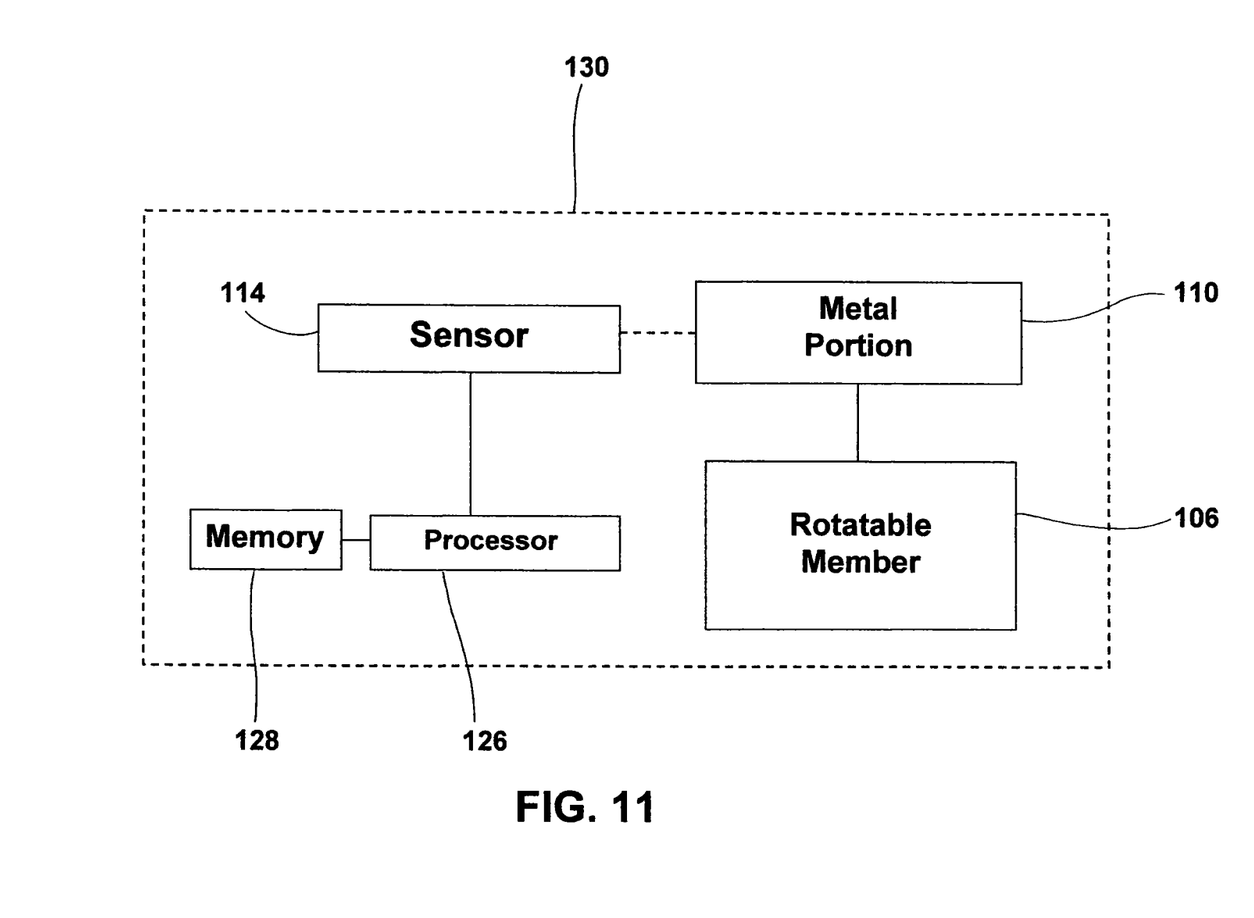
FIG. 11 is a box diagram of a sensor device according to an embodiment of the present invention.

In one embodiment, as seen in FIG. 11, the sensor 114, the metal portion 110, the rotatable member 106, and/or the processor 126 can form a sensor device 130. The sensor device 130 can be part of the prosthetic joint 102 and/or the prosthetic device 100. The sensor device 130 and its components can be used to determine the angle of the rotatable member 106 and subsequently the angle of the prosthetic joint 102.

For example, as seen in FIG. 3 and FIG. 6, the rotation of the rotatable member 106 increases or decreases a distance of a gap 132 between the sensor 114 and the metal portion 110. In FIG. 3, the gap 132 has a distance of d1, while in FIG. 6, the gap 132 has a distance of d2, which is greater than d1. Thus, the rotation of the rotatable member 106 increased the distance of the gap 132 between the sensor 114 and the metal portion 110. The increase or decrease of the distance of the gap 132 between the sensor 114 and the metal portion 110 increases or decreases an amount of metal material in the proximate location to the sensor 114. Furthermore, the amount of metal material in the proximate location to the sensor 114 correlates with the angle of the rotatable member 106 in an absolute monotonic function.

Since the metal portion 110 does not contact the sensor 114, the sensor 114 can be sealed or coated to protect the sensor 114 and/or the metal portion 110 from the environmental elements. Furthermore, as noted above, the housing 116 (FIGS. 7 and 8) can be environmentally sealed. This can increase a longevity of the sensor 114 and/or the metal portion 110. In additional, the protective seal or coating may allow the amputee to perform activities which may have previously been limited due to the fear of environmental exposure to the sensor 114 and/or the metal portion 110 such as construction, hiking, outings near water, and various sports.

If the sensor 114 includes the processor 126 as shown in FIG. 9, then the sensor 114 can determine the angle of the rotatable member 106 (FIG. 3) and subsequently the angle of the prosthetic joint 102 (FIG. 3) based on the metal material data indicating an amount of metal material detected by the sensor 114 in the proximate location. Otherwise, if the processor 126 is external to the sensor 114 as shown in FIG. 10, the processor 126 can receive the metal material data from the sensor 114 indicating an amount of metal material detected by the sensor 114. The processor 126 can determine based on the metal material data, the angle of the rotatable member 106 (FIG. 3) and subsequently the angle of the prosthetic joint 102 (FIG. 3).

Figure 12:
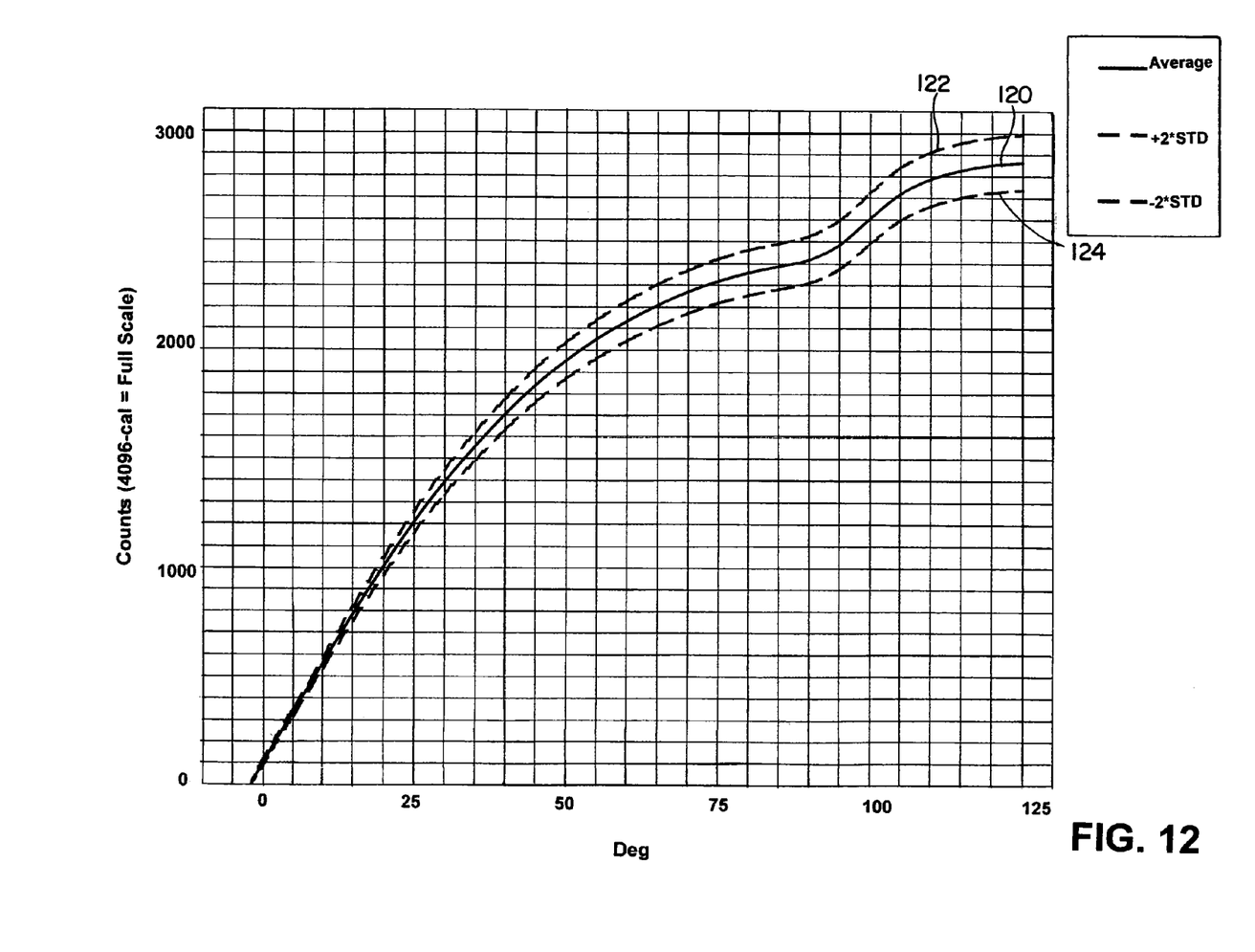
FIG. 12 is a graph of prosthetic joint angle versus digital step count according to an embodiment of the present invention.

This can be seen, for example, in the graph shown on FIG. 12 which can be stored in the memory 128. The counts on the Y-axis indicate an amount of metal material detected by the sensor 114, while the angle on the X-axis indicates an angle of the rotatable member 106. As seen in FIG. 12, the amount of the metal material detected by the sensor 114 can correspond to the angle of the rotatable member 106 based on an absolute monotonic function as indicated by a curve 120. A curve 122 and a curve 124 are depicted to indicate a standard deviation of the values of the curve 120. The curve 122 and the curve 124 can be used to determine error thresholds for the data detected by the sensor 114.

Although the monotonic function in FIG. 12 is non-linear, the monotonic function can also be linear. In one embodiment, the angle of the rotatable member 106 is the angle between the rotatable member 106 and the frame 104. In another embodiment, the angle of the rotatable member 106 indicates an angle of rotation between two positions. In yet another embodiment, the angle of the rotatable member 106 indicates an angle between a predetermined position and a current position of the rotatable member 106. In addition, although an absolute monotonic function is used, a relative monotonic function could also be used.

Thus, the processor 126 (FIG. 11) can utilize the graph shown on FIG. 12 to determine the angle of the rotatable member 106 and subsequently the angle of the prosthetic joint 102. Alternatively, the information presented in the graph in FIG. 12 can also be contained in a look-up table stored in the memory 128. In such a case, the processor in the sensor 114 or an external processor can utilize the look-up table to determine the angle of the prosthetic joint 102. In one embodiment, the sensor 114 can function as an absolute position sensor. Thus, when the sensor 114 and/or the prosthetic device 100 is activated, the sensor 114 and/or the processor 126 can immediately or substantially immediately determine an angle of the rotatable member 106 and/or the prosthetic joint 102. Thus, the rotatable member 106 and/or the prosthetic joint 102 does not have to move through any number of positions (like a repeating vernier scale), or store in memory a previous position and calculate movement from the previous position to determine the current angle of the rotatable member 106 and/or the prosthetic joint 102.

Although the prosthetic device 100 is shown as a prosthetic leg, the prosthetic device 100 can also be a prosthetic arm or other prosthetic body part. Thus, some or all of the components of the sensor device 130 can be part of the prosthetic arm or other prosthetic body part. Likewise, although the prosthetic joint 102 is shown as a prosthetic knee, the prosthetic joint 102 can also be, for example, a prosthetic ankle, a prosthetic elbow, a prosthetic wrist, or other type of joints which may require the use of prosthesis. Thus, some or all of the components of the sensor device 130 can be part of the prosthetic ankle, the prosthetic elbow, the prosthetic wrist, or other type of joints which may require the use of prosthesis. In addition, the sensor device 130 can also be used for artificial joints in addition to prosthetic joints, such as orthotic joints. Furthermore, the sensor device 130 can also detect a relative angle of the rotational objects in addition to the absolute angle.

In detecting the metal material, the proximate location for the sensor 114 can be, for example, a spherical shape. The spherical shape can be based on the location of the sensor 114. Furthermore the metal portion 110 can include, for example, a non-ferrous metal material or a combination of ferrous and non-ferrous metal material. The non-ferrous metal material can be, for example, aluminum. Since non-ferrous metal such as aluminum can be lighter than ferrous material, this can reduce a weight of the prosthetic joint 102 and/or the prosthetic device 100. The reduced weight of the prosthetic joint 102 and/or the prosthetic device 100 can allow smaller amputees to use the prosthetic joint 102 and/or the prosthetic device 100.

Figure 13:
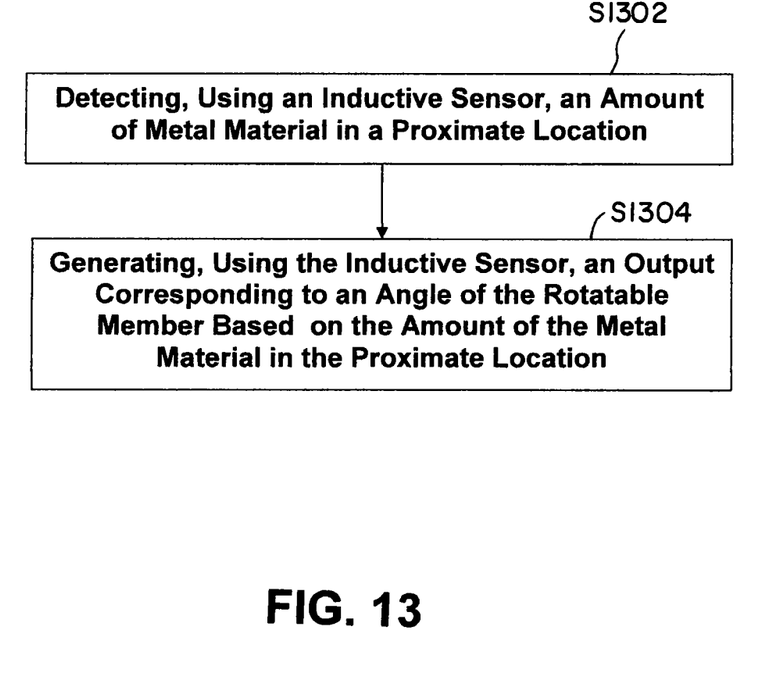
FIG. 13 depicts a process according to an embodiment of the present invention.

In one embodiment, the present invention can be a process as shown in FIG. 13. In Step S1302, an amount of metal material in a proximate location is detected using an inductive sensor. For example, the sensor 114 can detect an amount of metal portion 110 is present in a proximate location of the sensor 114. Furthermore, the sensor 114 can be, for example, an inductive sensor. In Step S1304, an output corresponding to an angle of the rotatable member based on the amount of the metal material in the proximate location is output using the inductive sensor. For example, the sensor 114 can generate metal material data indicating an amount of the metal portion 110 is present in the proximate location.

Although the metal portion 110 can form, for example, a cam as shown in FIG. 3, a metal portion 210 forming a wedge, or a metal portion 310 forming variable profile unit as shown in FIG. 14 and FIGS. 15-17, respectively, can be used.

Figure 14:
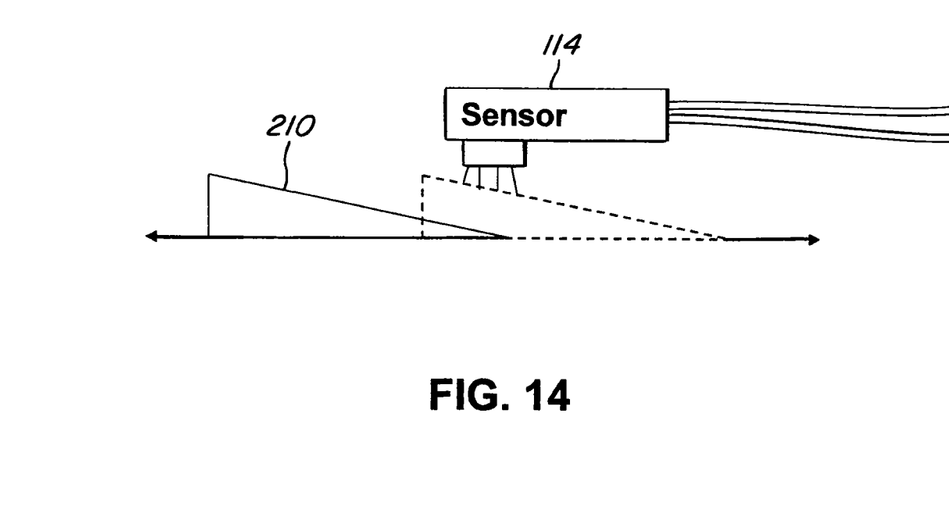
FIG. 14 depicts an inductive sensor detecting linear motion according to an embodiment of the present invention.

In FIG. 14, the sensor 114 can detect a translational position of an object. For example, in FIG. 14, the metal portion 210 forms a wedge, and the sensor 114 can determine an amount of metal material in the proximate location of the sensor 114. As the metal portion 210 slides past the sensor 114, an amount of metal material increases. Provided that the metal portion 210 does not slide past a point where there is a peak amount of the metal material, the amount of the metal material in the proximate location corresponds to the linear location of the metal portion 210. The amount of the metal material in the proximate location corresponds to the linear location of the metal portion 210 based on a monotonic function and such relationship can be stored, for example, in the memory 128 (FIG. 11). Thus, the sensor 114 can determine a translational location of the metal portion 210.

Figure 15:
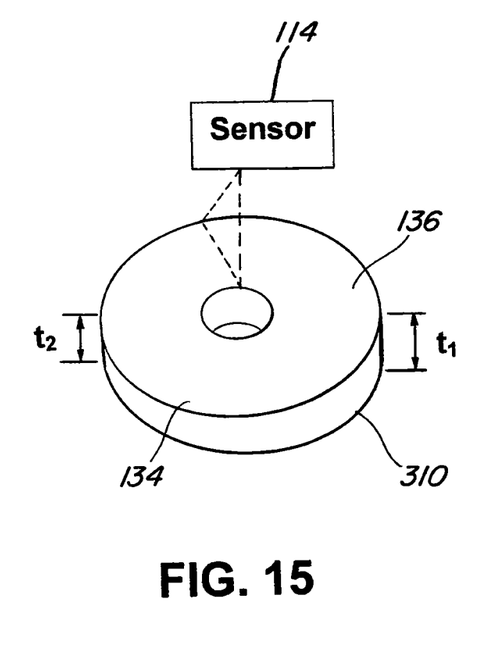
FIG. 15 depicts an inductive sensor and a variable profile unit according to an embodiment of the present invention.
Figure 16:
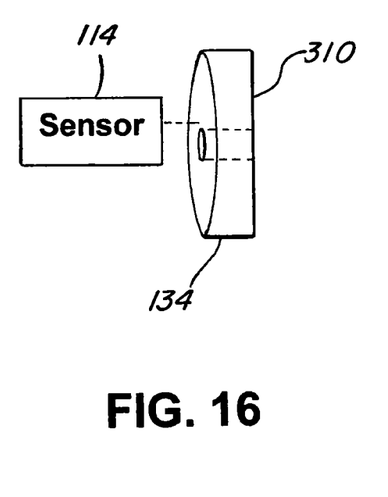
FIG. 16 depicts an inductive sensor and a variable profile unit according to an embodiment of the present invention.
Figure 17:
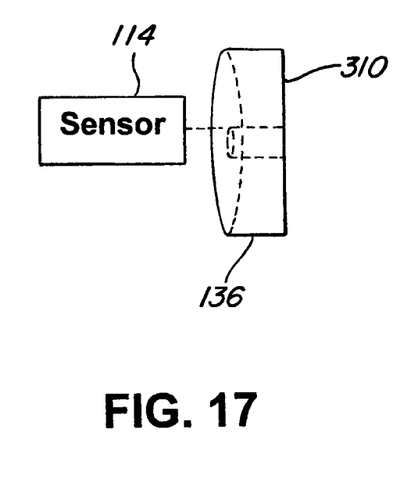
FIG. 17 depicts an inductive sensor and a variable profile unit according to an embodiment of the present invention.

In FIGS. 15-17, the sensor 114 can detect an amount of rotation of the metal portion 310. The metal portion 310 forms a variable profile unit, and the sensor 114 can determine an amount of metal material in the proximate location of the sensor 114. Thus, the metal portion 310 includes a thin portion 134 with a thickness of t2 and a thick portion 136 with a thickness of t1. The thickness t1 is greater than the thickness t2. For example, as the metal portion 310 is rotated, an amount of metal material in the proximate location of the sensor 114 increases as shown in FIGS. 16 and 17. In FIG. 16, the thin portion 134 is facing the sensor 114, while in FIG. 17 the thick portion 136 is facing the sensor 114. The amount of the metal material in the proximate location corresponds to the rotation of the metal portion 210 based on a function and such relationship can be stored, for example, in the memory 128 (FIG. 11). Thus, the sensor 114 can determine a rotation of the metal portion 210.

According to embodiments, aspects and implementations of the present disclosure may be useful for analysis of a variety of actions, activities, events, and phenomena. For example, embodiments may be used to analyze any rotation motion. Such information may be used to detect or predict activity that approaches the known limits of a system or device to avoid extension beyond said limits. Such information may also be used to determine appropriate action in response to adjust at least one of the factors contributing to rotational action. By further example, embodiments may be used to collect information about activity and environment during a gait cycle. For example, the rotation of portions of a leg, knee, arm, elbow, or other articulated member may be sensed and utilized in a system or device to track, react to, or respond to such readings. Responses may include the application of settings in a prosthetic knee to facilitate improved mobility of a user. Other joints and parts of the body may be benefited by embodiments of the present disclosure.

Those of ordinary skill would appreciate that the various illustrative logical blocks, modules, and algorithm steps described in connection with the examples disclosed herein may be implemented as electronic hardware, computer software, or combinations of both. Furthermore, the present invention can also be embodied on a machine readable medium causing a processor or computer to perform or execute certain functions.

To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosed apparatus and methods.

The various illustrative logical blocks, units, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the examples disclosed herein may be embodied directly in hardware, in a software module executed by a processor, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an Application Specific Integrated Circuit (ASIC). The ASIC may reside in a wireless modem. In the alternative, the processor and the storage medium may reside as discrete components in the wireless modem.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A sensor device for an artificial joint comprising:
a rotatable member;
a metal material connected to the rotatable member; and
an inductive sensor configured to detect an amount of the metal material in a proximate location to the inductive sensor, and to generate an output corresponding to an angle of the artificial joint based on the amount of the metal material in the proximate location, wherein a rotation of the rotatable increases or decreases a gap between the rotatable member and the inductive sensor to thereby vary the amount of the metal material in the proximate location.

2. The sensor device of claim 1 wherein the amount of the metal material in the proximate location corresponds to the angle of the artificial joint based on a monotonic function.

3. The sensor device of claim 1, wherein the rotatable member includes a cam, and wherein the gap is located between the cam and the inductive sensor.

4. The sensor device of claim 1 wherein the rotatable member includes a variable profile unit, and wherein the gap is located between the variable profile unit and the inductive sensor.

5. The sensor device of claim 1 wherein the metal material includes a non-ferrous metal material.

6. The sensor device of claim 5 wherein the non-ferrous metal material includes aluminum.

7. The sensor device of claim 1 wherein the rotatable member is a part of a prosthetic leg.

8. The sensor device of claim 1 wherein the rotatable member is a part of a prosthetic ankle.

9. The sensor device of claim 1 wherein the proximate location is a spherical shape based on a location of the inductive sensor.

10. A sensor device for a prosthetic joint comprising:
a rotatable member;
a non-ferrous metal material connected to the rotatable member; and an inductive sensor configured to detect an amount of the non-ferrous metal material in a spherical shape based on a location of the inductive sensor, and to generate an output corresponding to an angle of the prosthetic joint based on the amount of the metal material in the spherical shape,
wherein the amount of the non-ferrous metal material in the spherical shape corresponds to the angle of the prosthetic joint based on a monotonic function, and wherein a rotation of the rotatable member increases or decreases a gap between the rotatable member and the inductive sensor to thereby vary the amount of the non-ferrous metal material in the spherical shape.

11. The sensor device of claim 10 wherein the rotatable member includes a cam, and wherein the gap is located between the cam and the inductive sensor.

12. The sensor device of claim 10 wherein the rotatable member includes a variable profile unit, and wherein the gap is located between the variable profile unit and the inductive sensor.

13. The sensor device of claim 10 wherein the non-ferrous metal material includes aluminum.

14. The sensor device of claim 10 wherein the rotatable member is a part of a prosthetic leg.

15. The sensor device of claim 10 wherein the rotatable member is a part of a prosthetic ankle.

16. A method for determining an angle of a prosthetic joint including a rotatable member, the method comprising:
detecting, using an inductive sensor, an amount of metal material in a proximate location; and
generating, using the inductive sensor, an output corresponding to an angle of the prosthetic joint based on the amount of the metal material in the proximate location, wherein a rotation of the rotatable member increases or decreases a gap between the rotatable member and the inductive sensor to thereby vary the amount of the metal material in the proximate location.

17. The method of claim 16 wherein the amount of the metal material in the proximate location corresponds to the angle of the prosthetic joint based on a monotonic function.

18. The method of claim 16 wherein the metal material includes a non-ferrous metal material.

19. The method of claim 18 wherein the non-ferrous metal material includes aluminum.

20. The method of claim 16 wherein the proximate location is a spherical shape based on a location of the inductive sensor.

* * * * *